United States Patent [19]

Shiino et al.

[11] Patent Number: 4,981,596
[45] Date of Patent: Jan. 1, 1991

[54] SYSTEM FOR TREATING BLOOD FOR AUTOTRANSFUSION

[75] Inventors: Satoru Shiino, Kyoto; Masaki Shimotakahara, Osaka; Takesi Isozaki, Aichi; Masanobu Mimura, Hyogo; Kuniaki Takabayashi; Norikazu Hashimoto, both of Osaka, all of Japan

[73] Assignee: Green Cross Corporation, Osaka, Japan

[21] Appl. No.: 270,328

[22] Filed: Nov. 14, 1988

[30] Foreign Application Priority Data

Nov. 13, 1987 [JP] Japan .................................. 62-288205

[51] Int. Cl.$^5$ ............................................. B01D 13/00
[52] U.S. Cl. ..................................... 210/650; 210/780; 210/808; 210/198.1; 210/257.2; 210/258; 210/321.6; 210/321.87; 210/388; 210/406; 210/489; 210/492; 604/319; 604/406; 604/416

[58] Field of Search ............... 210/650, 651, 780, 785, 210/808, 188, 198.1, 256, 257.1, 257.2, 258, 321.6, 321.82, 321.83, 321.84, 321.86, 321.87, 446.1, 489, 492, 406, 388; 604/4, 416, 317, 406; 55/87, 178; 422/47

[56] References Cited

U.S. PATENT DOCUMENTS

| | | | |
|---|---|---|---|
| 4,137,307 | 1/1979 | Funakoshi et al. | 514/21 |
| 4,303,530 | 12/1981 | Shah et al. | 210/489 |
| 4,432,750 | 2/1984 | Estep | 604/403 |
| 4,690,762 | 9/1987 | Katsura | 210/457 |
| 4,744,785 | 5/1988 | Rosenthal et al. | 604/4 |

Primary Examiner—W. Gary Jones
Attorney, Agent, or Firm—Sughrue, Mion, Zinn, Macpeak & Seas

[57] ABSTRACT

A system for treating the blood of a patient, which is obtained by, for example, bleeding during an operation and thus to be autotransfused to the patient, as well as a device therefor is disclosed. The process comprises sucking the blood under a sucking pressure of 80 to 150 mmHg, filtering the sucked blood through a filter membrane of a pore size of 100 to 150 μm and storing the filtered blood in a storage tank while shaking.

12 Claims, 1 Drawing Sheet

SYSTEM FOR TREATING BLOOD FOR AUTOTRANSFUSION

FIELD OF THE INVENTION

This invention relates to a system for treating the blood of a patient, which is obtained by, for example, copious bleeding during an operation and thus to be autotransfused to the patient. More particularly, it relates to a process and apparatus for treating a blood for autotransfusion which comprises filtering the blood and shaking the same as well as a device therefor.

BACKGROUND OF THE INVENTION

Recently there have been attempted various techniques for utilizing blood obtained by copious bleeding during an operation. These techniques include filtration through a filter membrane, adsorption with a resin, centrifugation and fractionation.

However, there remain a number of problems to be solved in these techniques, for example, the need of an expensive device and/or a complicated procedure and the acceleration of bleeding with the use of a large amount of an anticoagulant.

SUMMARY OF THE INVENTION

Under these circumstances, the inventors have conducted extended studies to solve the above problems. As a result, the inventors have found that the blood of a patient can be safely and effectively returned to said patient by a relatively simple process with the use of a relatively simple device, which comprises sucking the whole blood into a storage tank provided with a filtration device that vibrates or shakes. Subsequently, the inventors have conducted further studies to thereby confirm the present invention.

An object of the present invention is to provide a process for treating a blood for autotransfusion which comprises sucking the blood obtained by, for example, bleeding under a sucking pressure of 80 to 150 mmHg; filtering said blood through a filter membrane of a pore size of 100 to 150 μm; and storing the filtered blood while it is being shaken.

Another object of the present invention is to provide a device for conducting the above process which comprises:

(1) an inlet means for collecting the blood from a patient;
(2) a returning tube for returning the blood to the patient;
(3) a means for filtering the sucked blood;
(4) a storage tank for collecting and storing the filtered blood;
(5) a shaker for shaking the storage tank; and
(6) a vacuum means for maintaining the storage tank under reduced pressure.

DETAILED DESCRIPTION OF THE INVENTION

Figure 1:
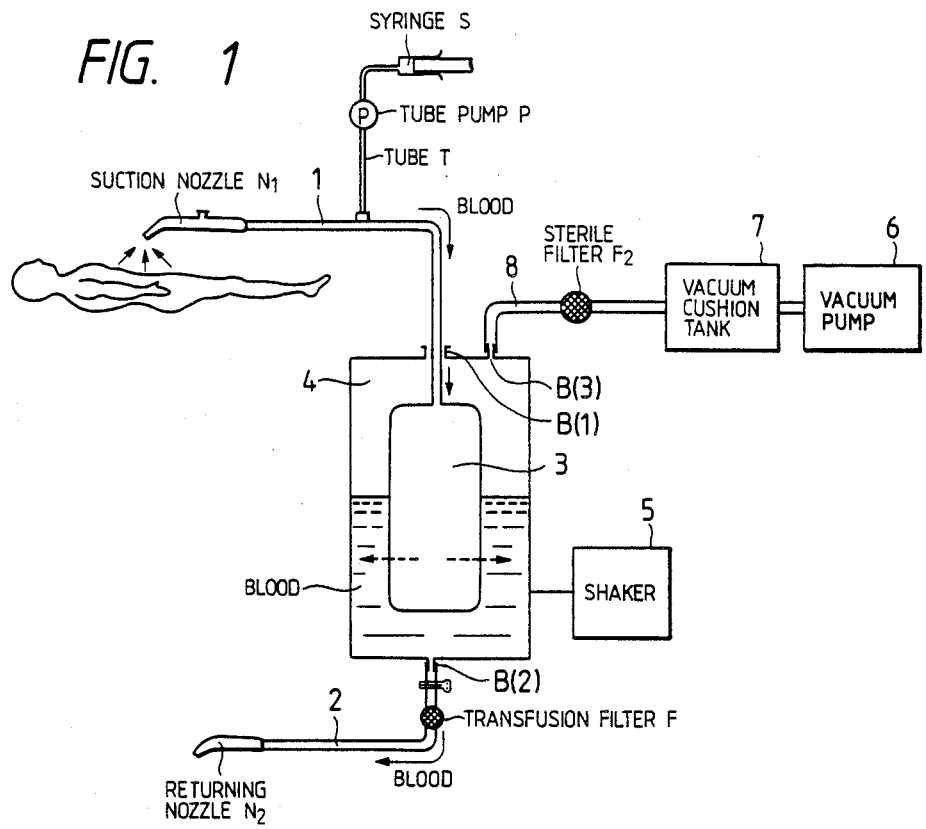
FIG. 1 diagrammatically illustrates the autotransfusion device of the present invention.

Referring now to the drawings, the present invention will be further illustrated, though it is not restricted thereby.

FIG. 1 diagrammatically illustrates the autotransfusion device of the present invention.

It is preferable that an inlet tube 1 for collecting the blood is made of a material which is sufficiently flexible and would not induce any toxic reaction. Preferable examples thereof include resins, in particular, vinyl chloride resins. This inlet tube may be optionally provided with a component for adding various drugs, for example, an anticoagulant such as sodium citrate or heparin, an antihemolytic agent such as polyoxyethylene/polypropylene copolymer or an agent for treating free-hemoglobin such as haptoglobin. Examples of this component include a tube T provided with a syringe S and a tube pump P. Alternately, the anticoagulant may be preliminarily fed into the storage tank 4.

In order to further facilitate the collection of the bleeding blood, a suction nozzle $N_1$ may be provided at the tip of the sucking tube. It is preferable that the suction nozzle $N_1$ is made of a resin, in particular, a polyvinyl chloride resin or a polyalkylene resin such as a polypropylene resin.

It is preferable that a returning tube 2 is made of a material which is sufficiently flexible and would not induce any toxic reaction. Preferable examples thereof include resins, in particular, vinyl chloride resins. This returning tube may be optionally provided with a known component for intravenous injection such as a transfusion filter F. Furthermore, a returning nozzle $N_2$ may be provided at the tip of the tube. It is preferable that the returning nozzle $N_2$ is made of a resin, in particular, a polyvinyl chloride resin or a polyalkylene resin such as a polyprolylene resin.

The sucked blood is filtered prior to the storage. A filtration device 3 is employed therefor.

Figure 2:
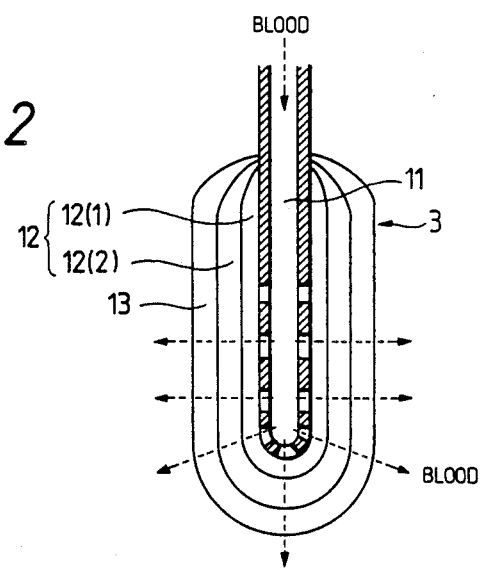
FIG. 2 is a sectional view of a filtration device to be used in the present invention.

As shown in FIG. 2, the filtration device 3 has a multilayered bag structure. It comprises, from the center outward toward the external layer, a core 11; a defoaming device 12, preferably consisting of two defoaming nets 12-1 and 12-2; and a filter membrane 13.

It is preferable that the core 11 is made of a resin, in particular, a polyvinyl chloride resin.

It is preferable that the defoaming net(s), which are provided in order to inhibit foaming at the sucking, are made of a foamable polyurethane resin. It is further preferable to coat the core with two or more defoaming nets which are located, from the inside to the outside, in order of pore size. The device of the present invention as shown in FIG. 2 involves two defoaming nets differing in pore size from each other.

It is preferable that the defoaming net 12-1 has approximately 5 to 10 pores/cm$^2$ while the defoaming net 12-2 has approximately 11 to 15 pores/cm$^2$.

It is preferable that the filter membrane 13 is made of polyester fibers and has a pore size of approximately 100 to 150 μm, more preferably approximately 120 μm.

The sucked blood is transported from the core 11 to the storage tank 4 via the defoaming nets 12-1 and 12-2 and the filter membrane 13.

The storage tank 4 is employed for storing the filtered blood. Either a hard type tank or a soft type one may be employed therefor. It may be made of, for example, a vinyl chloride resin, an acrylic resin or a polycarbonate resin. It has a capacity of, for example, 500 to 2,000 ml.

The storage tank 4 may be further provided with a component for feeding such drugs as cited above, for example, a drug inlet, not illustrated.

The storage tank 4 is provided with connecting parts B(1), B(2) and B(3) for connecting to the inlet tube 1, the returning tube 2 and the reducing tube 8 respectively. Through the connecting part B(1), the inlet tube 1 is connected to the filtration device 3 which is provided at the inside of the storage tank 4.

A shaker (hemolator) 5 is employed for shaking the storage tank 4 to thereby inhibit the coagulation of the blood stored therein.

The shaking may be effected by, for example, a swinging pendulum motion of the maximum swing angle of approximately 50 to 90° and a swinging rate of approximately 0.1 to 10 sec.

A vacuum pump 6 is employed for maintaining the storage tank 4 under a reduced pressure. It should provide a sucking pressure of 80 to 150 mmHg, preferably approximately 100 mmHg.

A vacuum cushion tank 7 is employed for maintaining the storage tank 4 under a sucking pressure of approximately 80 to 150 mmHg. A sucking pressure exceeding 150 mmHg might cause hemolysis. On the other hand, that lower than 80 mmHg cannot fully exert the desired sucking effect.

A reducing tube 8 is employed for reducing the pressure within the storage tank, together with the vacuum pump 6 and the vacuum cushion tank 7. It is preferable that this reducing tube is made of a vinyl chloride resin.

The reducing tube 8 may be further provided with a sterile filter $F_2$. It is preferable that the vacuum cushion tank 7, the vacuum pump 6 and the shaker 5 of the device of the present invention are not exchanged for each patient but fixed while other components are disposable.

The process for autotransfusion with the use of the device of the present invention will now be illustrated.

The bleeding blood of a patient is sucked under a sucking pressure of approximately 80 to 150 mmHg and fed into the filtration device 3 via the inlet tube 1. When this procedure is continuously carried out, the sucking rate is approximately 1 to 2 l/min. It is preferable that an antihemolytic agent such as polyoxyethylene/polyoxypropylene copolymer is successively added to the blood during sucking. The amount of the antihemolytic agent to be added ranges from 10 to 100 ml of a 10% (w/v) solution thereof per 500 ml of the blood. The antihemolytic agent is usually added from the syringe S via the tube T.

The sucked blood is then filtered in the filtration device 3 under a similar sucking pressure to the one described above. The filtered blood is collected and stored in the storage tank 4. When sucking is intermittently conducted, the total period of time required for collecting 500 ml of the blood ranges from approximately ten minutes to two hours.

It is preferable that the inside of the storage tank 4 is preliminarily primed with a transfusion media such as Saviosol ® (mfd. by Green Cross Corporation; lactic acid Ringer solution containing 4% (w/v) of dextran of a molecular weight of 40,000) prior to the sucking. After discharging the transfusion, the tubes of the device of the present invention may be disposed.

It is preferable that an anticoagulant is preliminarily fed into the storage tank 4. An example of the anticoagulant is sodium citrate. The anticoagulant may be added in an amount of 20 to 40 ml of a 4% (w/v) solution thereof per 500 ml of the blood.

Further various drugs such as an antihemolytic agent may be injected into the inlet tube via the tube T. In this case, the preparation for the injection should be effected prior to the initiation of the injection.

Then, the injection is to be started. The vacuum pump 6, the shaker 5 and the tube pump P are operated by a switch.

During the collection step, the storage tank 4 is shaken with the shaker 5, for example, maintained at a temperature in the range of 20° to 37° C. for ten minutes to five hours.

After collecting 500 to 1,000 ml of the blood, it is preferable to determine the amount of free hemoglobin in the blood by a method according to, for example, JP-A-Nos. 54-150885, 54-150886 or 54-158995 (the term "JP-A" herein used means an "unexamined published Japanese patent application"). It is further preferable to add a treating agent in an amount corresponding to the determined hemoglobin. An example of the treating agent is haptoglobin, which may be prepared by a method disclosed in, for example, U.S. Pat. No. 4,137,307 corresponding to British Pat. No. 1,426,039, U.S. Pat. No. 4,061,735 and JP-A-No. 50-111496. The haptoglobin may be added in an amount of 1 to 2 U/mg of free hemoglobin. The treating agent may be either fed into the storage tank 4 or injected into the body of the patient via a separate system at the autotransfusion.

The blood thus collected can be administered, i.e., autotransfused to the patient by a known intravenous injection method.

It is preferable to administer, for example, an antibiotic to the patient in order to prevent infection.

To illustrate the present invention in detail, the following examples are given but are not construed to limit the scope of the present invention.

EXAMPLE

The following components were employed:

inlet nozzle $N_1$: a suction tube made of polyvinyl chloride, Argyle ® of MAR-type, mfd. by Nippon Sherwood Co.;

inlet tube 1: made of soft polyvinyl chloride, 10 mm (o.d.)×6.6 mm (i.d.)×2,500 mm (length), mfd. by Maeda Sangyo K.K.;

returning tube 2: a transfusion set mfd. by Terumo Co., made of polyvinyl chloride, provided with a transfusion filter;

filtration device 3:

core 11: made of polyvinyl chloride, a hole of 10 mm in diameter is formed in a semihard side wall;

defoaming net 12-1: made of polyurethane foam, #13, 50 mm (o.d.)×30 mm (i.d.), mfd. by Neumo Kogyo K.K.;

defoaming net 12-2: made of polyurethane foam, #7, 70 mm (o.d.)×50 mm (i.d.), mfd. by Neumo Kogyo K.K.;

filter membrane 13: made of polyester, pore size—120 μm, mfd. by Maeda Sangyo K.K.;

The core is coated with the baggy defoaming net (#13), the defoaming net (#7) and the filter membrane in this order and the tip is fixed with a resin;

storage tank 4: made of polyvinyl chloride, 114 mm (diameter)×235 mm (length), capacity —ca·1,800 ml, two hose nipples for connecting to the inlet tube and the vacuum cushion tube, respectively, are provided at the upper part while one for connecting the returning tube is provided at the lower part;

shaker 5: a wiper motor No. 859100-2390 mfd. by Asmo Co.;

vacuum pump 6: diaphragm DA-l5S type, mfd. by Shinkuki Kogyo K.K.;

vacuum cushion tank 7: made of acrylic resin, 90 mm (o.d.)×80 mm (i.d.)×140 mm (height), capacity —ca. 650 ml, three hose nipples for gauce and for connecting the vacuum pump and the storage tank respectively and a vacuum valve are provided at the upper part;

reducing tube 8: made of polyvinyl chloride, the same as 1; and sterile filter: a membrane filter for air, Millex® FG 50 mfd. by Millipore Co. or Advantec 50TRO 50AN mfd. by Toyo Roshi K.K.

These components were connected to thereby construct the device of the present invention.

Thus approximately 1,500 ml of the blood of a patient was collected by sucking the same under a sucking pressure of 100 mmHg and treated for one minute.

TEST EXAMPLE 1

With the use of the device of Example, 200 ml of the blood of a patient was sucked under a sucking pressure of 100 mmHg and fed into the storage tank. Table 1 shows the composition of the blood thus stored in the storage tank.

The control shown in Table 1 was the blood of the same patient which was not treated according to the process of the present invention.

TABLE 1

| Blood component | Control | Invention |
| --- | --- | --- |
| Total serumprotein (g/dl) | 5.6 | 4.6 |
| Sodium (mEq/l) | 138 | 156 |
| Potassium (mEq/l) | 3.8 | 4.7 |
| Chlorine (mEq/l) | 103 | 102 |
| Leukocyte count (cells/$\mu$l) | 4,700 | 5,000 |
| Erythrocyte count ($10^4$ cells/$\mu$l) | 370.0 | 331.0 |
| Hemoglobin (g/dl) | 11.5 | 10.8 |
| Hematocrit (%) | 34.8 | 30.9 |
| Platelet count ($10^4$ cells/$\mu$l) | 17.3 | 4.7 |
| Prothrombin (%) | 50.2 | 34.8 |
| Partial thromboplastin (sec) | 86.8 | 103.8 |
| Fibrinogen (mg/dl) | 332.7 | 204.7 |
| Factor II (%) | 90.7 | 75.6 |
| Factor VIII (%) | 154.2 | 85.9 |
| Factor IX (%) | 118.3 | 83.7 |
| Factor X (%) | 75.5 | 62.7 |
| Free hemoglobin ($\mu$g/dl) | 3.4 | 660 |
| Haptoglobin (mg/dl) | 260 | 279 |
| Hemogram: | | |
| stab cell (%) | 4.0 | 6.0 |
| segmented cell (%) | 55.0 | 42.0 |
| lymphocyte (%) | 36.0 | 49.0 |
| monocyte (%) | 5.0 | 3.0 |

The system of the present invention can give the following effects:

(1) The coagulation of the blood can be inhibited since the blood is sucked and stored while shaking the storage tank.

(2) The addition of a trace amount of an antihemolytic agent and the low sucking pressure ranging from 80 to 150 mmHg substantially inhibit the hemolysis caused by sucking and elevate the sucking efficiency.

(3) Although the blood in the storage tank shows an elevated level of hemoglobin, this level can be normalized by adding a treating agent such as haptoglobin thereto. Thus, the autotransfusion can be conducted without any trouble.

(4) The process of the present invention makes it possible to readily and efficiently conduct autotransfusion, compared with known methods.

While the invention has been described in detail and with reference to specific embodiments thereof, it will be apparent to one skilled in the art that various changes and modifications can be made therein without departing from the spirit and scope thereof.

What is claimed is:

1. A process for treating blood for autotransfusion comprising the steps of: removing blood from a patient obtained by bleeding under a sucking pressure in the range of 80 to 150 mmHg; filtering the sucked blood through a filter membrane of 100 to 150 $\mu$m in pore size and storing the filtered blood; and shaking the stored filtered blood.

2. A process for treating blood for autotransfusion as set forth in claim 1, further comprising adding an antihemolytic agent to the sucked blood.

3. A process for treating blood for autotransfusion as set forth in claim 1, further comprising adding haptoglobin to the collected blood.

4. A process for treating blood for autotransfusion as set forth in claim 1, further comprising the step of adding an anticoagulant while said blood is stored.

5. A process for treating blood for autotransfusion as set forth in claim 1, wherein the rate of blood removal from the patient is in the range of 1–2 l/min.

6. An autotransfusion device comprising:
an inlet means for collecting blood from a patient;
means for filtering the collected blood;
a storage tank for collecting and storing the filtered blood;
means for inhibiting coagulation of the stored blood comprising a shaker for shaking the storage tank;
vacuum means for maintaining the storage tank under a reduced pressure; and
a returning tube for returning the blood to the patient.

7. The device of claim 6 wherein said inlet means comprises a suction nozzle made of a polyvinyl chloride resin or a polyalkylene resin and an inlet tube made from vinyl chloride resin.

8. The device of claim 6 wherein said filtration means comprises a core receiving said blood, defoaming means surrounding said core and a filter membrane surrounding said defoaming means.

9. The device of claim 8 wherein said defoaming means comprises a pair of defoaming nets of different pore size.

10. The device of claim 9 wherein one of said defoaming nets has a pore density in the range of 5–10 pores/cm$^2$ and the other of said defoaming nets has a pore density in the range of 11–15 pores/cm$^2$.

11. The device of claim 8 wherein said filter membrane has a pore size in the range of 100–150 $\mu$m.

12. The device of claim 6 wherein said vacuum means comprises a vacuum pump, a vacuum cushion tank for maintaining said storage tank under a predetermined pressure and a pressure reducing tube coupling said storage tank to said vacuum cushion tank.

* * * * *